United States Patent
Jeon et al.

(10) Patent No.: US 9,341,656 B2
(45) Date of Patent: May 17, 2016

(54) NANOSENSORS INCLUDING GRAPHENE AND METHODS OF MANUFACTURING THE SAME

(71) Applicant: Samsung Electronics Co., Ltd., Suwon-si, Gyeonggi-do (KR)

(72) Inventors: Tae-han Jeon, Hwaseong-si (KR); Joo-ho Lee, Hwaseong-si (KR); Jeo-young Shim, Yongin-si (KR); Dong-ho Lee, Seongnam-si (KR); Kun-sun Eom, Seoul (KR); Hee-jeong Jeong, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 226 days.

(21) Appl. No.: 13/846,304

(22) Filed: Mar. 18, 2013

(65) Prior Publication Data
US 2014/0062454 A1     Mar. 6, 2014

(30) Foreign Application Priority Data
Aug. 29, 2012    (KR) .......................... 10-2012-0095171

(51) Int. Cl.
| | | |
|---|---|---|
| *G01N 27/00* | (2006.01) |
| *G01R 19/00* | (2006.01) |
| *G01N 33/487* | (2006.01) |
| *B82Y 15/00* | (2011.01) |

(52) U.S. Cl.
CPC ...... *G01R 19/0092* (2013.01); *G01N 33/48721* (2013.01); *B82Y 15/00* (2013.01)

(58) Field of Classification Search
CPC ...... G01R 19/0092; G01R 7/00; G01R 31/26; H01L 23/544; H01L 21/68; G01N 33/48721; B82Y 15/00

USPC ......... 324/71.1, 654–692; 257/213, 288, 295, 257/77, 253, 48, 797; 204/601–630; 438/292, 48, 49; 506/38; 73/760; 219/162

See application file for complete search history.

(56) References Cited

U.S. PATENT DOCUMENTS

| | | | | |
|---|---|---|---|---|
| 6,413,792 | B1 * | 7/2002 | Sauer et al. | ..................... 438/49 |
| 7,619,257 | B2 * | 11/2009 | Pfeiffer | ......................... 257/76 |

(Continued)

FOREIGN PATENT DOCUMENTS

| | | |
|---|---|---|
| KR | 1020120000343 A | 1/2012 |
| KR | 101119913 B1 | 2/2012 |

(Continued)

OTHER PUBLICATIONS

Bell et al., "Precision Cutting and Patterning of Graphene with Helium Ions," *Nanotechnology*, 20: 1-5 (2009).

(Continued)

*Primary Examiner* — Arleen M Vazquez
*Assistant Examiner* — Steven Yeninas
(74) *Attorney, Agent, or Firm* — Leydig, Voit & Mayer, Ltd.

(57) ABSTRACT

Nanosensors including graphene and methods of manufacturing the same. A nanosensor includes a first insulating layer in which a first nanopore is formed; a graphene layer that is disposed on the first insulating layer and having a second nanopore or a nanogap formed therein adjacent to the first nanopore; and a marker element that is disposed adjacent to the graphene layer and identifies a position of the graphene layer.

13 Claims, 12 Drawing Sheets

(56) References Cited

U.S. PATENT DOCUMENTS

| | | |
|---|---|---|
| 2006/0154399 A1* | 7/2006 | Sauer et al. ............... 438/48 |
| 2010/0255623 A1* | 10/2010 | Huang ..................... 438/51 |
| 2010/0327847 A1* | 12/2010 | Leiber et al. ............ 324/71.1 |
| 2011/0114918 A1* | 5/2011 | Lin et al. ................ 257/24 |
| 2012/0037919 A1 | 2/2012 | Xu et al. |
| 2012/0193236 A1* | 8/2012 | Peng et al. .............. 204/603 |
| 2012/0193237 A1* | 8/2012 | Afzali-Ardakani et al. .. 204/627 |
| 2012/0326732 A1* | 12/2012 | Cho et al. ............... 324/654 |
| 2013/0037410 A1* | 2/2013 | Xu et al. ................ 204/601 |
| 2013/0256139 A1* | 10/2013 | Peng ..................... 204/630 |
| 2014/0349892 A1* | 11/2014 | Van Der Zaag et al. ....... 506/38 |

FOREIGN PATENT DOCUMENTS

| | | |
|---|---|---|
| WO | WO 2011/046706 A1 | 4/2011 |
| WO | WO 2012/005857 A1 | 1/2012 |

OTHER PUBLICATIONS

Lu et al., "In Situ Electronic Characterization of Graphene Nanoconstrictions Fabricated in a Transmission Electron Microscope," *Nano Letters*, 11: 5184-5188 (2011).

Venkatesan et al., "Stacked Graphene-Al2O3 Nanopore Sensors for Sensitive Detection of DNA and DNA Protein Complexes," *ACS Nano*, 6(1): 441-450 (2012).

* cited by examiner

NANOSENSORS INCLUDING GRAPHENE AND METHODS OF MANUFACTURING THE SAME

CROSS-REFERENCE TO RELATED APPLICATION

This application claims the benefit of Korean Patent Application No. 10-2012-0095171, filed on Aug. 29, 2012, in the Korean Intellectual Property Office, the disclosure of which is incorporated herein by reference in its entirety.

BACKGROUND

1. Field

The present disclosure relates generally to nanosensors and methods of manufacturing the same, and more particularly to nanosensors including markers and methods of manufacturing the nanosensors.

2. Description of the Related Art

The Maxam-Gilbert method and the Sanger method are two methods used to determine the order of bases of deoxyribonucleic acid (DNA). The Maxam-Gilbert method is a method of determining the order of bases of DNA by randomly performing cleavage at specific bases and separating DNA strands having different lengths using electrophoresis. The Sanger method is a method of determining the order of bases of DNA by synthesizing a complementary DNA strand by putting a template DNA, a DNA polymerase, a primer, a normal deoxynucleotide triphosphate (dNTP), and a dideoxynucleotide triphosphate (ddNTP) together into a tube. When the ddNTP is added while the complementary DNA strand is synthesized, DNA synthesis is terminated, to thus obtain complementary DNAs having different lengths, so that the order of bases of DNA may be determined by separating the complementary DNA strands using electrophoresis. However, such methods used to determine the order of bases of DNA are time and effort-consuming. Accordingly, studies on a new next generation DNA sequencing method for determining the order of bases of DNA have recently been actively conducted.

Methods of analyzing the order of bases of DNA using a graphene nanogap electrode and a graphene nanopore electrode are desirable.

SUMMARY

Provided are nanosensors, including graphene, which may be easily formed and methods of manufacturing the nanosensors. Also provided are nanosensors including markers for identifying a position of graphene and methods of manufacturing the nanosensors.

In particular, the provided nanosensors and methods have advantages in that a nanogap or a nanopore having a resolution equal to or less than about 0.34 nm may be manufactured, one base of DNA may be analyzed, electron mobility is high, and the order of bases can be measured.

Additional aspects will be set forth in part in the description which follows and, in part, will be apparent from the description, or may be learned by practice of the presented embodiments.

According to an embodiment, a nanosensor includes: a first insulating layer having a first pore formed therein; a graphene layer disposed on the first insulating layer and having a second pore or a gap formed therein adjacent to the first pore; and a marker element, disposed adjacent to the graphene layer, that identifies a position of the graphene layer. In certain aspects, a gap is different from a pore in that a gap divides a graphene layer into two or more distinct regions, whereas a pore does not and may be completely surrounded by the graphene layer.

In certain aspects, a size of the first pore is equal to or greater than a size of the second pore or a size of the gap. In certain aspects, the second pore or the gap partially may overlap the first pore. In certain aspects, the marker element is disposed on a portion of the first insulating layer where the graphene layer is not formed such that the marker is spaced apart from the graphene layer. In certain aspects, the marker element includes a first marker and a second marker that are spaced apart from each other with the graphene layer therebetween.

In certain aspects, a line that connects the first marker and the second marker crosses the graphene layer, and in certain aspects, the line that connects the first marker and the second marker passes through the second pore or the gap.

In certain aspects, each of the first marker and the second marker are spaced apart by about 50 nm to about 500 nm from the second pore or the gap. In certain aspects, the marker element is formed of a metal material, an insulating material, or a polymer. In certain aspects, the marker element has a stepped shape formed by etching a portion of the first insulating layer.

In certain aspects, the nanosensor further includes a first electrode pad and a second electrode pad that are respectively disposed on opposite sides of the graphene layer and spaced apart from each other.

In certain aspects, the marker element is disposed on the graphene layer. In certain aspects, the marker element includes a first marker and a second marker that are disposed on a portion of the graphene layer where the first electrode pad and the second electrode pad are not formed such that the first marker and the second marker are spaced apart from each other with the second pore or the gap therebetween.

In certain aspects, the nanosensor further includes a second insulating layer that covers the first electrode pad and the second electrode pad and is disposed on the first insulating layer. In certain aspects, the marker element is disposed on the second insulating layer. In certain aspects, the marker element includes a first marker and a second marker that are disposed on a portion of the second insulating layer where the second insulating layer does not overlap the graphene layer such that the first marker and the second marker are spaced apart from each other with the second pore or the gap therebetween.

In certain aspects, the marker element includes a first marker and an second marker that are disposed on a portion of the second insulating layer where the second insulating layer overlaps the graphene layer such that the first marker and the second marker are spaced apart from each other with the second pore or the gap therebetween.

According to another embodiment, a method of manufacturing a nanosensor includes: sequentially forming a first insulating layer, a graphene layer, and a metal layer on a substrate; patterning the graphene layer and the metal layer; forming a marker element on the first insulating layer or the graphene layer; forming a second insulating layer on the first insulating layer to cover the patterned graphene layer and metal layer and the marker; and forming a gap or a pore in the graphene layer.

In certain aspects, the forming of the gap or the pore includes forming the gap or the pore using a transmission electron microscope (TEM) or a focused ion beam (FIB) tool. In certain aspects, the marker element includes a first marker and a second marker that are spaced apart from each other with the gap or the pore therebetween. In certain aspects, the forming of the marker element includes forming the marker element using FIB or electron beam lithography.

According to yet another embodiment, a method of forming a marker on an apparatus including a graphene layer includes: forming an element of the apparatus; forming the graphene layer on a first portion of the element; forming a marker on a second portion of the element or the graphene layer; and forming one or more other elements of the apparatus.

BRIEF DESCRIPTION OF THE DRAWINGS

These and/or other aspects will become apparent and more readily appreciated from the following description of the embodiments, taken in conjunction with the accompanying drawings in which:

FIGS. 8A through 11 are plan views illustrating nanosensors each having a gap, according to other embodiments of the present disclosure.

DETAILED DESCRIPTION

Figure 1A:
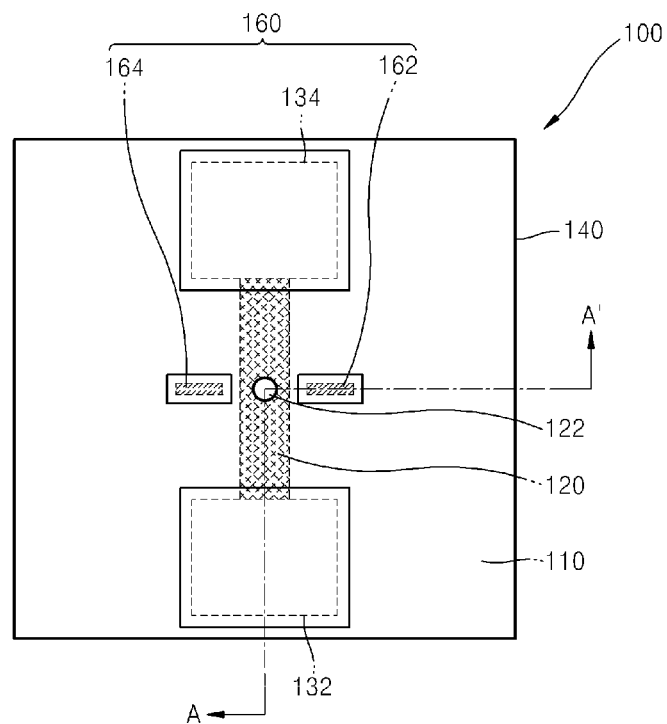
FIG. 1A is a plan view illustrating a nanosensor according to an embodiment of the present disclosure.

Various embodiments will now be described more fully with reference to the accompanying drawings, in which exemplary embodiments are shown. In the drawings, the same reference numerals denote the same elements, and sizes or thicknesses of the elements may be exaggerated for clarity. The following embodiments are exemplary and various modifications may be made therein.

Figure 1B:
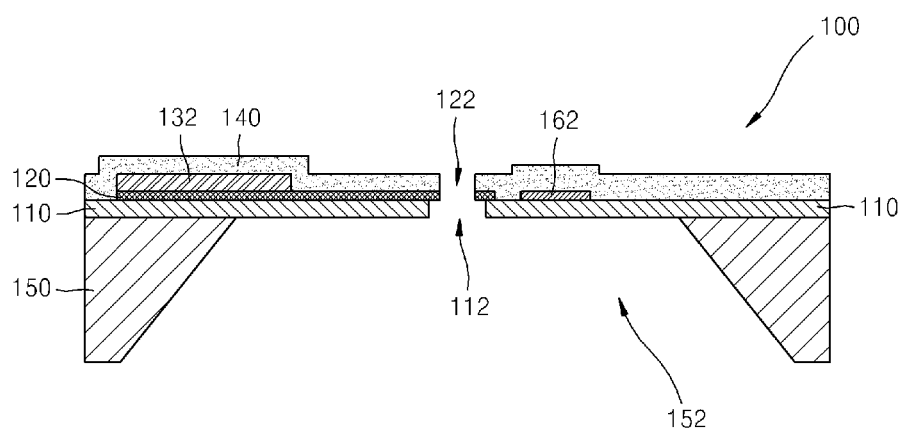
FIG. 1B is a cross-sectional view taken along line A-A' of the nanosensor of FIG. 1A.

FIG. 1A is a plan view illustrating a nanosensor 100 according to an embodiment. FIG. 1B is a cross-sectional view taken along line A-A' of the nanosensor 100 of FIG. 1A.

Referring to FIGS. 1A and 1B, the nanosensor 100 includes a first insulating layer 110 in which a first pore (e.g., nanopore) 112 is formed, and a graphene layer 120 that is disposed on the first insulating layer 110 and has a second pore (e.g., nanopore) 122 formed therein proximal to the first pore 112.

The first insulating layer 110 may be formed of a nitride, for example, silicon nitride (SiN). The first insulating layer 110 may be formed as a thin film having a thickness equal to or less than about tens of nanometers (nm). That is, a thickness of the first insulating layer 110 may range from about 10 nm to about 100 nm. When the first insulating layer 110 is formed of a nitride, the first pore 112 as will be explained below may be easily formed.

The first pore 112 may be formed in the first insulating layer 110. A size of the first pore 112 may be determined according to a size of a target molecule to be detected or sequenced. The first pore 112 may have a diameter on the order of nanometers or on the order of micrometers (μm). For example, a diameter of the first pore 112 may range from about one or several nm to tens of μm, for example, from about 1 nm to about 100 nm, from about 1 nm to about 5 nm, from about 1 nm to about 10 nm, from about 5 nm to about 10 nm, from about 1 nm to about 25 nm, or from about 10 nm to about 10 μm. A shape of the first pore 112 is not limited to that shown in FIG. 1B, and may be a circular shape, an oval shape, a polygonal shape, or other shape.

The first pore 112 may be formed by using, for example, an electron beam using a transmission electron microscope (TEM), or an ion beam using focused ion beam (FIB) or reactive ion etching (RIE) techniques.

The graphene layer 120 is formed on the first insulating layer 110. The graphene layer 120 may have a width equal to or less than about 100 nm, for example. Graphene is an allotrope of carbon whose structure is a one-atom-thick planar sheet of $sp^2$-bonded carbon atoms that are densely packed in a honeycomb crystal lattice. Graphene is a conductive material and a single graphene layer has a thickness of, for example, about 0.34 nm. Graphene, which is a structurally and chemically stable excellent conductor, has higher charge mobility than silicon (Si) and may enable more current to flow than copper (Cu). In particular, a thickness of one graphene layer 120 is similar to a size of one base constituting DNA. Accordingly, a target molecule may be more accurately identified.

The second pore 122 is formed in the graphene layer 120. The second pore 122 may be disposed adjacent to the first pore 112. A size of the second pore 122 may be determined according to a size of the target molecule to be detected or sequenced. A size of the second pore 122 may be equal to or less than a size of the target molecule, and may exceed a size of another molecule other than the target molecule. Accordingly, the target molecule is filtered by the second pore 122. Also, a size of the second pore 122 may be equal to or less than a size of the first pore 122, and the second pore 122 may partially overlap the first pore 112. For example, a diameter of the second pore 122 may range from several nm to tens of nm. A shape of the second pore 122 is not limited to that shown in FIG. 1B, and may be a circular shape, an oval shape, a polygonal shape or other shape. The second pore 122 may also be formed by using, for example, an electron beam using a TEM, or an ion beam using FIB or RIE techniques.

In the nanosensor 100 constructed as described above, when the target molecule stops up or is within the second pore 122, an electric field in the first pore 112 is changed, and a voltage is accordingly changed, and thus the target molecule is detected or sequenced. Accordingly, the graphene layer 120 acts as an electrode for measuring a change in an electric field in the first pore 112.

In an embodiment, a first electrode pad 132 and a second electrode pad 134 are formed on opposite sides of the graphene layer 120 relative to the second pore 122 and spaced apart from each other. An interval or distance between the first electrode pad 132 and the second electrode pad 134 is greater than a diameter of the second pore 122. In one embodiment, to more efficiently apply a voltage or current from an external power source to the graphene layer 120, a contact area between each of the first and second electrode pads 132 and 134 and the graphene layer 120 may be maximized. Each of the first electrode pad 132 and the second electrode pad 134 may have a polygonal shape such as a quadrangular shape as shown in FIG. 1A. However, the present embodiment is not limited thereto, and each of the first electrode pad 132 and the second electrode pad 134 may have any of various other shapes. Each of the first electrode pad 132 and the second electrode pad 134 may be formed of a conductive material, for example, a conductive material including gold (Au), chromium (Cr), copper (Cu), nickel (Ni), cobalt (Co), iron (Fe), silver (Ag), aluminum (Al), titanium (Ti), palladium (Pd), or a mixture thereof.

In addition, a second insulating layer 140 may be formed on the first insulating layer 110 to cover the first electrode pad 132 and the second electrode pad 134. The second insulating layer 140 prevents a short-circuit of the graphene layer 120 and first and second electrode pads 132 and 134 with respect to the outside. The second insulating layer 140 disposed over the graphene layer 120 may be formed of an oxide, for example, a material selected from the group consisting of $SiO_2$, $Al_2O_3$, $TiO_2$, $BaTiO_3$, $PbTiO_3$, $HfO_2$, and a mixture thereof. A thickness of the second insulating layer 140 may range from about 10 nm to about 500 nm or greater.

A substrate 150 that supports the first insulating layer 110 may be further disposed under the first insulating layer 110. An opening 152 may be formed in the substrate 150. The opening 152 may have a tapered structure that narrows in an upward direction as shown in FIG. 1B. Accordingly, the opening 152 may be connected to the first pore 112 and the second pore 122.

The opening 152 may be formed by using wet etching, for example, potassium hydroxide (KOH), tetramethylammonium hydroxide (TMAH), or buffer oxide etching (BOE) techniques. The opening 152 may have a diameter equal to or less than hundreds of micrometers (μm). For example, a diameter of the opening 152 may range from several μm to about 490 μm, and more specifically, may range from about 10 μm to about 100 μm. The opening 152 may be formed by using selective etching.

The substrate 150 may be formed of a semiconductor material or a polymer material. Examples of suitable semiconductor material include Si, germanium (Ge), GaAs, and GaN, and examples of suitable polymer material include an organic polymer and an inorganic polymer. Alternatively, the substrate 150 may be formed of quartz, glass, or the like.

Although not shown in FIGS. 1A and 1B, a dielectric layer may be further disposed between the substrate 150 and the first insulating layer 110. When the first insulating layer 110 is thin, current may flow between the substrate 150 and the graphene layer 120. Accordingly, in order to prevent current from flowing between the substrate 150 and the graphene layer 120, the dielectric layer may be selectively disposed between the substrate 150 and the first insulating layer 110.

The nanosensor 100 in certain embodiments further includes a marker element 160 that is disposed adjacent to the graphene layer 120 and which identifies a position of the graphene layer 120. The marker element 160 may be disposed on a portion of the first insulating layer 110 where the graphene layer 120 is not formed such that the marker element 160 is spaced apart from the graphene layer 120. For example, the marker element 160 may include a first marker 162 and a second marker 164 spaced apart from each other with the graphene layer 120 therebetween. A line that connects the first marker 162 and the second marker 164 may cross the graphene layer 120. For example, the line that connects the first marker 162 and the second marker 164 may pass through the second pore 122. Each of the first marker 162 and the second marker 164 may have, but is not limited to, a bar shape having a long width parallel to the direction of the line that connects the first marker 162 and the second marker 164. A distance between the second pore 122 and each of the first and second markers 162 and 164 is greater than a diameter of the second pore 122. For example, each of the first and second markers 162 and 164 may be spaced apart by about 50 nm to about 500 nm from the second pore 122. For example, each of the first and second markers 162 and 164 may be spaced apart by about 50 nm, about 100 nm, or about 500 nm from the second pore 122.

The marker element 160 may be formed of a metal material, an insulating material, or a polymer. In an embodiment, a suitable metal material includes a metal selected from the group consisting of Au, Cu, Pd, Ni, Ti, Cr, Fe, Co, platinum (Pt), and ruthenium (Ru).

An element of the nanosensor 100 is formed, for example, by using electron beam lithography, and then a nanopore is formed by using equipment such as an FIB tool or a TEM. In particular, a TEM is often used to form a pore having a size equal to or less than several nm. In this case, it is difficult to identify a position of the graphene layer 120. Accordingly, the marker element 160 is additionally formed in order to identify a position of the graphene layer even when a pore having a size of several nm is formed. The marker element 160 may be spaced apart by a distance equal to or less than hundreds of nm from the graphene.

Figure 2A:
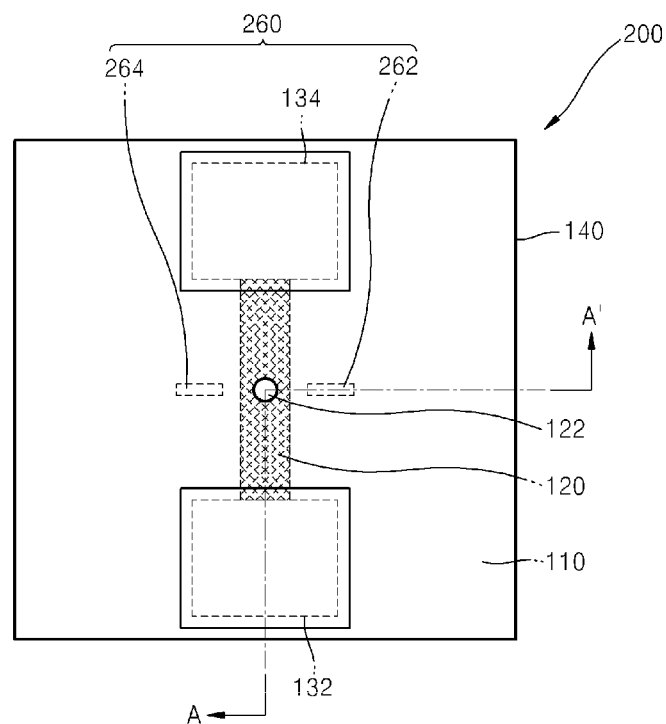
FIGS. 2A and 2B are, respectively, a plan view and a cross-sectional view illustrating a nanosensor according to another embodiment of the present disclosure.
Figure 2B:
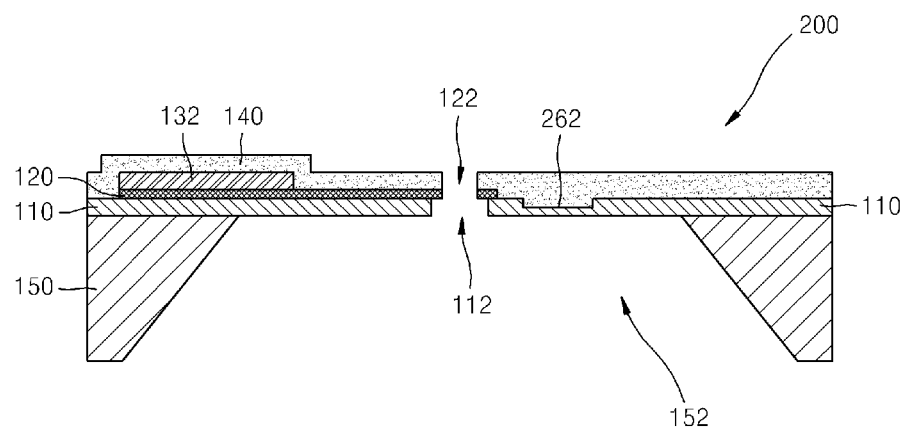

A marker may be formed in any of various positions other than that shown in FIGS. 1A and 1B. FIGS. 2A and 2B are, respectively, a plan view and a cross-sectional view illustrating a nanosensor 200 according to another embodiment.

When FIGS. 1A and 1B are compared with FIGS. 2A and 2B, elements other than a marker 260 are the same. Accordingly, an explanation of the same elements will not be given. Referring to FIGS. 2A and 2B, the marker 260 includes a stepped shape formed by etching a portion of the first insulating layer 110. That is, the marker 260 may be formed on a portion of the first insulating layer 110 where the graphene layer 120 is not formed by etching a portion of the first insulating layer 110 so that marker 260 is spaced apart from the graphene layer 120. For example, the marker 260 may include a third marker 262 and a fourth marker 264 that are spaced apart from each other with the graphene layer 120 therebetween. A line that connects the third and fourth markers 262 and 264 may cross the graphene layer 120. For example, the line that connects the third and fourth markers 262 and 264 may pass through the second pore 122. Each of the third and fourth markers 262 and 264 may have, but is not limited to, a bar shape having a long width parallel to the direction of the line that connects the third and fourth markers 262 and 264. Since the marker 260 is formed by etching the first insulating layer 110, a material for forming the marker 260 does not need to be additionally stacked on insulating layer 110.

Figure 3A:
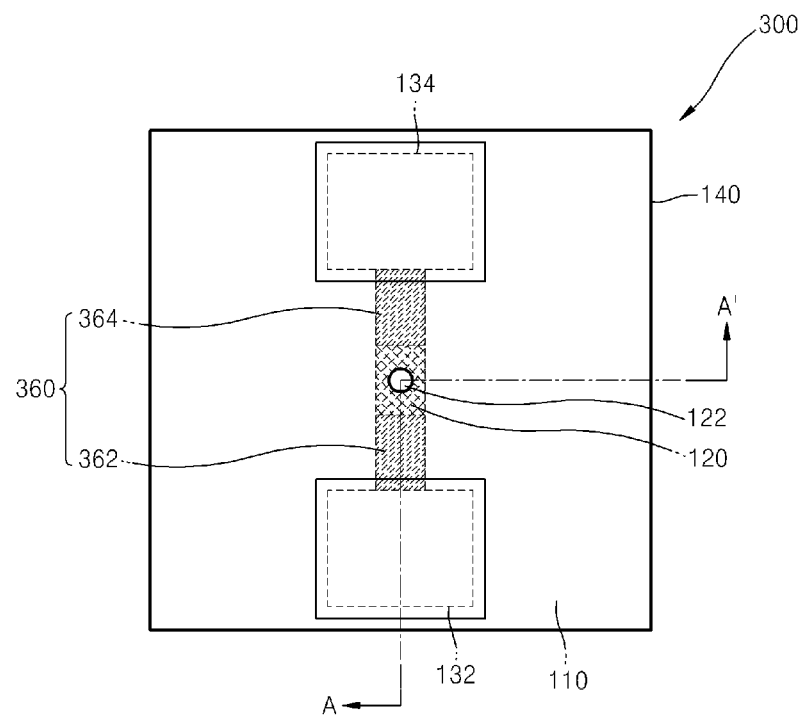
FIGS. 3A and 3B are, respectively, a plan view and a cross-sectional view illustrating a nanosensor according to another embodiment of the present disclosure.
Figure 3B:
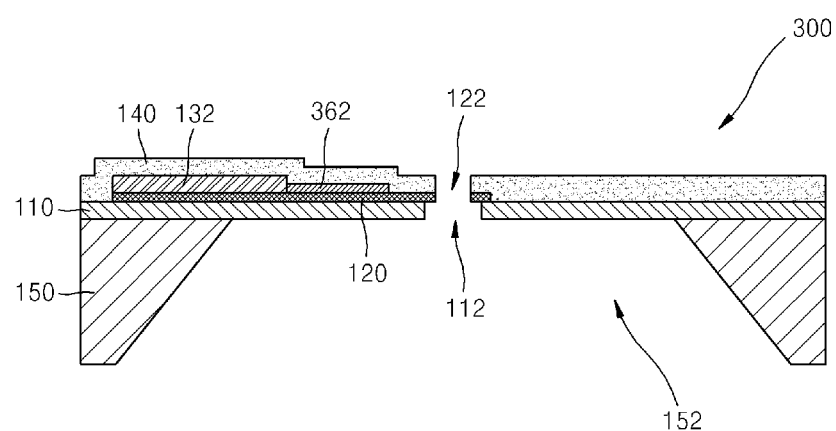

FIGS. 3A and 3B are, respectively, a plan view and a cross-sectional view illustrating a nanosensor 300 according to another embodiment. Referring to FIGS. 3A and 3B, a marker 360 is formed on the graphene layer 120. For example, the marker 360 may include a fifth marker 362 and a sixth marker 364 that are formed on a portion of the graphene layer 120 where the first and second electrode pads 132 and 134 are not formed such that the fifth marker 362 and the sixth marker 364 are spaced apart from each other with the second pore 122 disposed therebetween. An interval between the fifth marker 362 and the sixth marker 364 is greater than a size of the second pore 122. Accordingly, a size of the second pore 122 is not limited by the fifth and sixth markers 362 and 364. The marker 360 may be formed of a metal material, an insulating material, or a polymer. Accordingly, the marker 360 and the first and second electrode pads 132 and 134 are distinguishable from each other.

Figure 4:
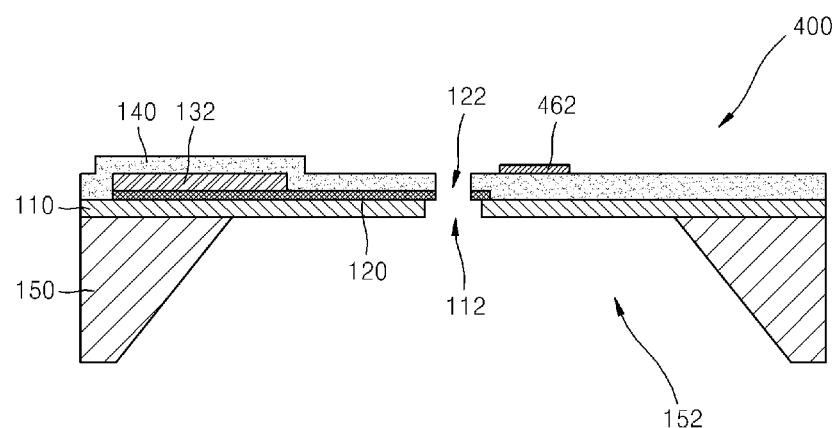
FIGS. 4 and 5 are cross-sectional views illustrating nanosensors according to other embodiments of the present disclosure.
Figure 5:
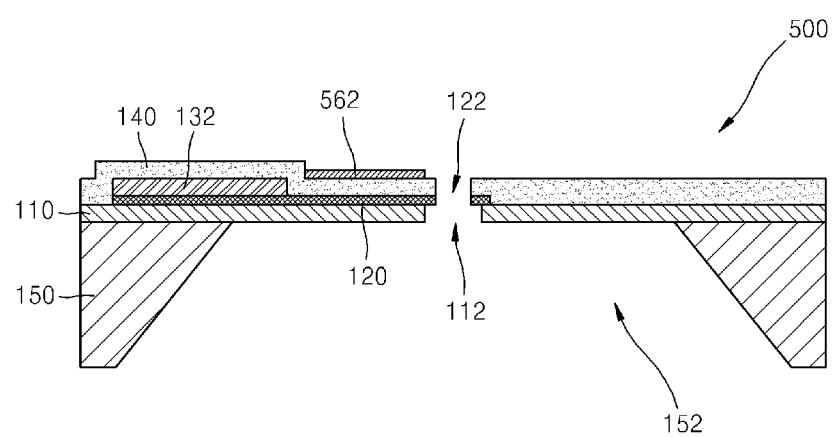

Alternatively, a marker may be formed on the second insulating layer 140. FIGS. 4 and 5 are cross-sectional views illustrating a nanosensor 400 and a nanosensor 500, respectively, according to other embodiments. Referring to FIG. 4, a marker 460 (only a seventh marker 462 is shown and an eighth marker 464 is not shown) may be formed on a portion of the second insulating layer 140 that does not overlap the graphene layer 120. For example, the marker 460 may include a seventh marker 462 and an eighth marker 464 (not shown) that are spaced apart from each other with the graphene layer 120 disposed therebetween. A line that connects the seventh and eighth markers 462 and 464 may cross the graphene layer 120. For example, the line that connects the seventh and eighth markers 462 and 464 may pass through the second pore 122. Each of the seventh and eighth markers 462 and 464 may have, but is not limited to, a bar shape having a long width along the line that connects the seventh and eighth markers 462 and 464. The marker may be formed of a metal material, an insulating material, or a polymer.

Alternatively, referring to FIG. 5, a marker (only a ninth marker 562 is shown and a tenth marker 564 is not shown) may be formed on a portion of the second insulating layer 140 where the second insulating layer 140 overlaps the graphene layer 120. For example, the marker may be formed on a portion of the second insulating layer 140 where the second insulating layer 140 does not overlap the first and second electrode pads 132 and 134 (the second electrode pad 134 is not shown) and where the second insulating layer 140 overlaps the graphene layer 120. The marker may be formed of a metal material, an insulating material, or a polymer.

A method of manufacturing the nanosensor 100 of FIGS. 1A and 1B will now be explained. FIGS. 6A through 6F are cross-sectional views for explaining a method of manufacturing the nanosensor 100 including graphene, according to an embodiment.

Figure 6A:
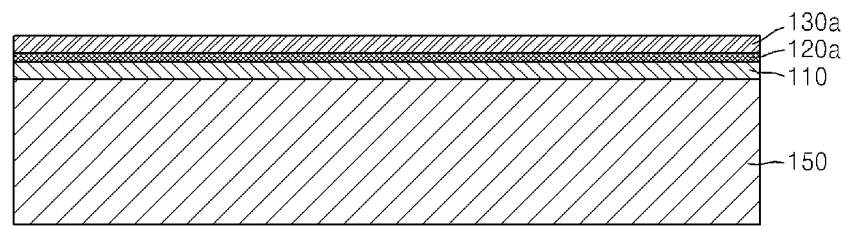
FIGS. 6A through 6F are cross-sectional views for explaining a method of manufacturing the nanosensor including graphene of FIGS. 1A and 1B, according to an embodiment of the present disclosure.

Referring to FIG. 6A, the first insulating layer 110 formed of an insulating material, a graphene layer 120a, and a metal layer 130a are sequentially stacked on the substrate 150. The substrate 150 may be a substrate formed of any of various materials such as a semiconductor substrate or a polymer substrate. For example, when the substrate 150 is a Si substrate, the substrate 150 may be prepared by polishing the Si substrate to a predetermined thickness, for example, about 300 μm, by using chemical mechanical polishing (CMP) or the like. Although not shown in FIG. 6A, an etch mask layer for forming a predetermined opening may be further disposed on a bottom surface of the substrate 150. The first insulating material 110 may be formed of a silicon oxide or a silicon nitride. The graphene layer 120a may be formed on the first insulating layer 110 by using a transfer technique Next, the metal layer 130a is formed on the graphene layer 120a. The metal layer 130a may be formed of a material having high electrical conductivity such as Au, Cu, Ag, or Al.

Figure 6B:
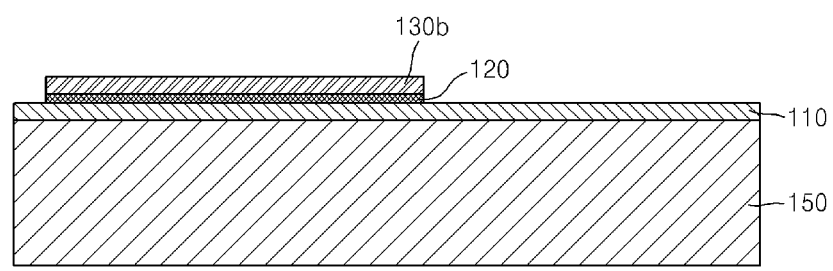

Referring to FIG. 6B, the metal layer 130a and the grapheme layer 120a are patterned. The metal layer 130a may be patterned by using photolithography and etching. For example, a photoresist layer may be disposed on the metal layer 130a and may be patterned to obtain a patterned photoresist layer. Next, the metal layer 130a may be etched by using the patterned photoresist layer as an etch mask. In addition, an exposed portion of the graphene layer 120a is etched by using an additionally patterned photoresist layer as an etch mask.

Alternatively, the metal layer 130a may be patterned by using a lift-off technique. A photoresists layer is disposed on the graphene layer 120a and is patterned, for example, by using electron beam lithography or photolithography. In this case, the patterning is performed such that only photoresist on a portion where the metal layer 130a may remain is removed. The metal layer 130a is stacked on the photoresist layer and photoresist lift-off is performed to form a metal layer 130b on grapheme layer 120a. An exposed portion of the graphene layer 120a is etched, for example, by using an additionally patterned photoresist layer as an etch mask. Alternatively, an exposed portion of the graphene layer 120a is etched by using the metal layer 130b as an etch mask.

Figure 6C:
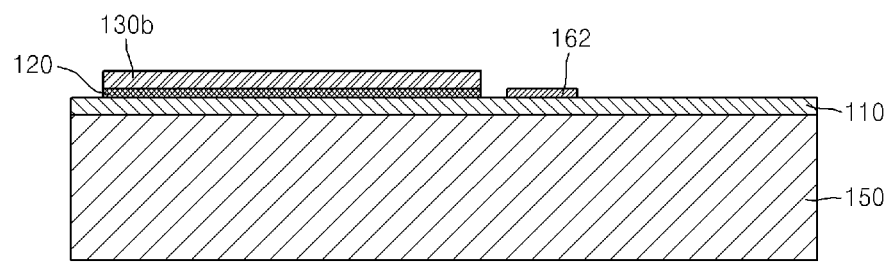

Referring to FIG. 6C, the marker element 160 (only the first marker 162 is shown and the second marker 164 is not shown) is formed on an exposed portion of the first insulating layer 110. The marker element 160 may be patterned by using electron beam lithography. For example, an electron beam resist (ER) sensitive to an electron beam is coated or deposited on the first insulating layer 110, and the electron beam resist (ER) is patterned by applying an electron beam such that a portion of the first insulating layer 110 having a marker shape is exposed. A material corresponding to the marker element 160 is formed on the exposed portion of the first insulating layer 110 and the electron beam resist (ER). The material corresponding to the marker element 160 may be a metal material, an insulating material, or a polymer. Next, when the electron beam resist (ER) is removed, for example by using a lift-off technique, the material formed on the electron beam resist (ER) is also removed.

Figure 6D:
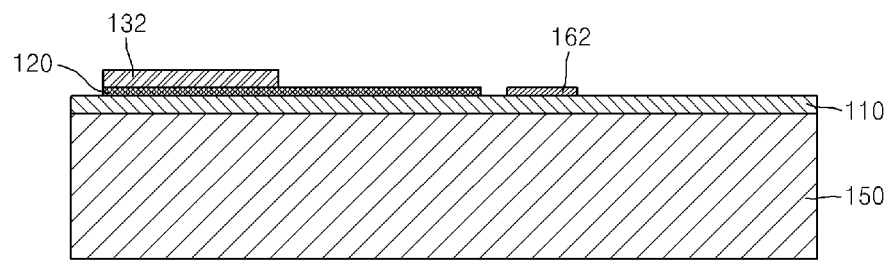
Figure 6E:
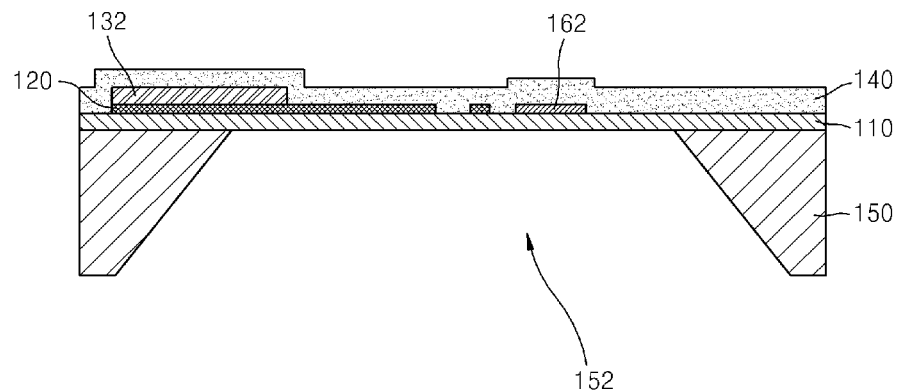

Referring to FIG. 6D, a portion of the metal layer 130b is etched to form the first and second electrode pads 132 and 134 (the second electrode pattern 134 is not shown) and expose a portion of the graphene layer 120. Referring to FIG. 6E, the second insulating layer 140 is formed on the first insulating layer 110 to cover the first and second electrode pads 132 and 134 (pad 134 not shown), the graphene layer 120, and the marker element 160, and the opening 152 is formed in the bottom surface of the substrate 150, for example by using an etching technique or the like.

Figure 6F:
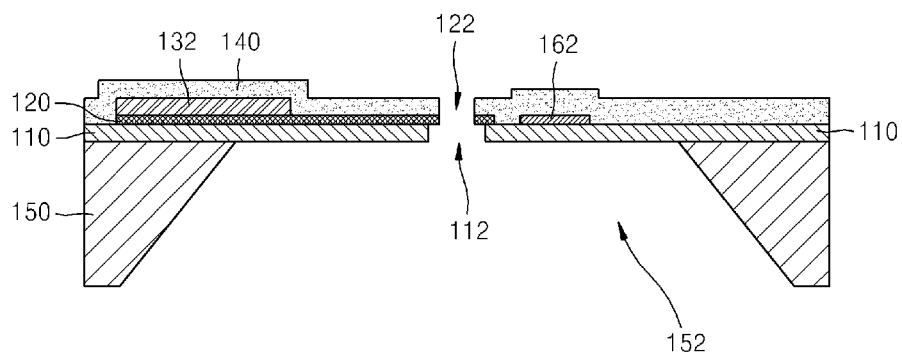

Referring to FIG. 6F, the first and second pores 112 and 122 are formed, thereby forming the nanosensor 100. The first and second pores 112 and 122 are formed to be adjacent to or connected to the opening 152, and may be formed by using equipment such as an FIB tool or a TEM. When a pore is formed by using an FIB tool or a TEM, it is difficult to identify a position of the graphene layer 120. However, since the marker element 160 is formed adjacent to the graphene layer 120, it is known that the graphene layer 120 is disposed in a space between the first and second markers 162 and 164. Accordingly, the first and second pores 112 and 122 is formed in the middle of the space between the first and second markers 162 and 164. A size of the second pore 122 may be equal to or less than a size of the first pore 112, and a diameter of the second pore 122 may be a few or several nm or greater. A shape of each of the first and second pores 112 and 122 is not limited to that shown in FIG. 6F, and may be a circular shape, an oval shape, a polygonal shape or other shape.

Although the marker element 160 is formed by using electron beam lithography in FIG. 6C, the present embodiment is not limited thereto. The marker element 160 may be formed otherwise, such as by milling an insulating material through FIB, or marker element 160 may be formed by using photolithography or electron beam lithography techniques. Alternatively, the marker element 160 may be formed by stacking a metal material or an insulating material by using an electron beam or an ion beam of an FIB tool.

FIGS. 6A through 6F are cross-sectional views for explaining a method of manufacturing the nanosensor 100 of FIGS.

1A and 1B. In the nanosensors 200, 300, 400, and 500 shown in FIGS. 2A through 5A, each marker may also be formed by using electron beam lithography or FIB. In this case, however, a method of forming a marker or an order in which the marker is formed may vary according to a position of the marker.

Such a marker may be applied to the nanosensor 100 using a gap (e.g., nanogap). A nanosensor including a nanogap detects or sequences a target molecule by measuring tunneling current when the target molecule passes through the nanogap. A nanogap is formed in a portion of a graphene layer that is used as an electrode. A first insulating layer and the graphene layer are separated by the nanogap. A gap is different from a pore in that a gap divides a graphene layer into a plurality of regions. As can be seen in FIG. 1A, for example, graphene layer 120 surrounds the entire periphery of circular-shaped pore 122, whereas in FIG. 7A, for example, graphene layer 120 only contacts on two sides of the rectangular-shaped gap 124.

Figure 7A:
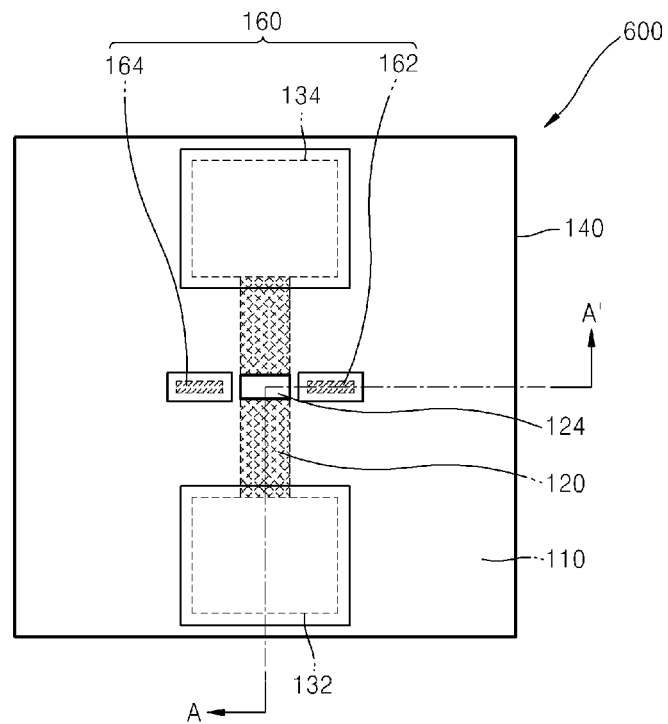
FIGS. 7A and 7B are, respectively, a plan view and a cross-sectional view illustrating a nanosensor having a gap, according to an embodiment of the present disclosure.
Figure 7B:
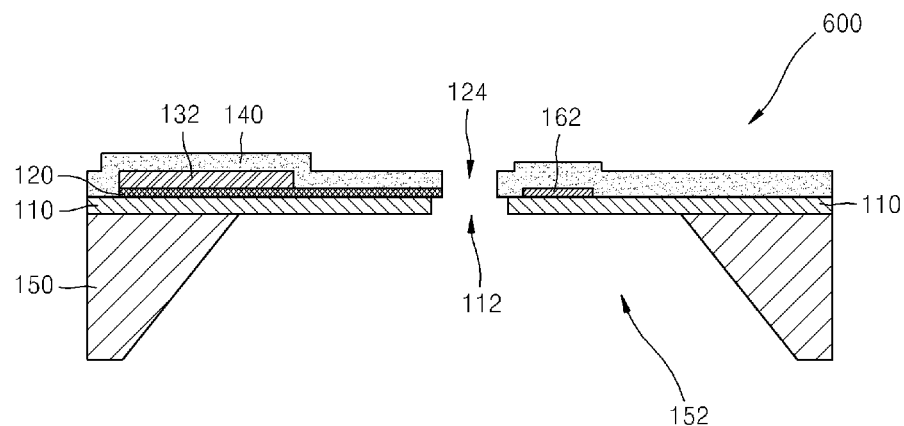
Figure 8A:
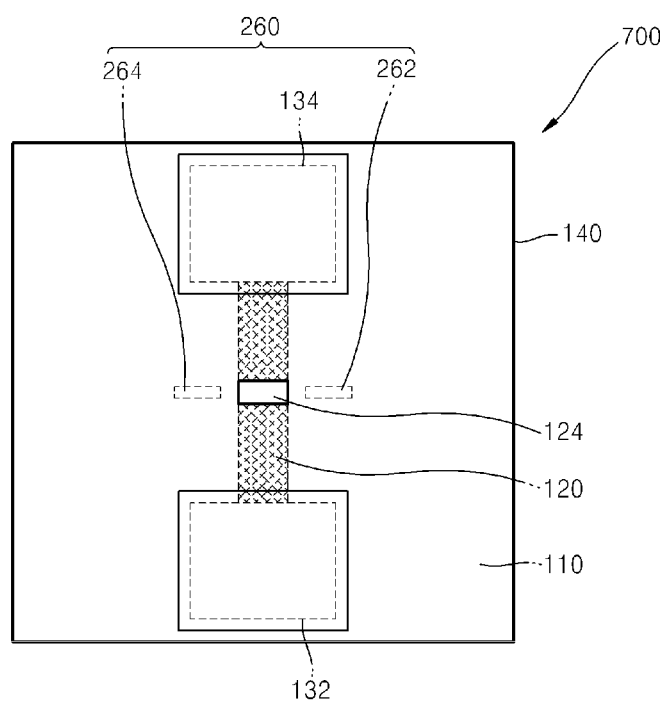
Figure 9:
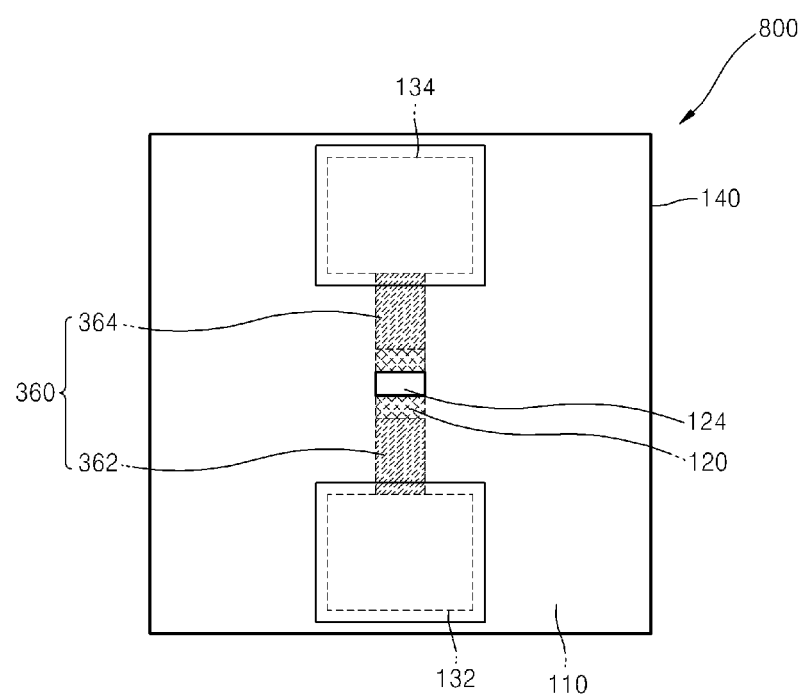
Figure 10:
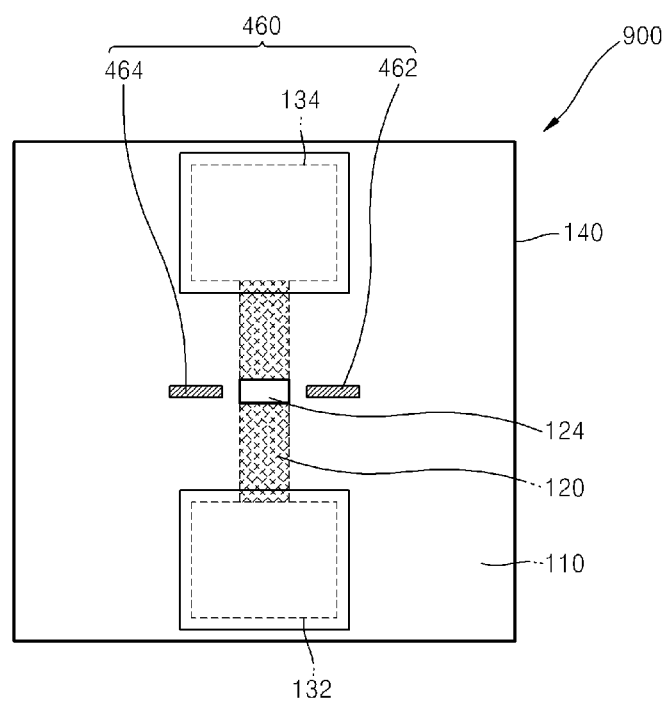
Figure 11:
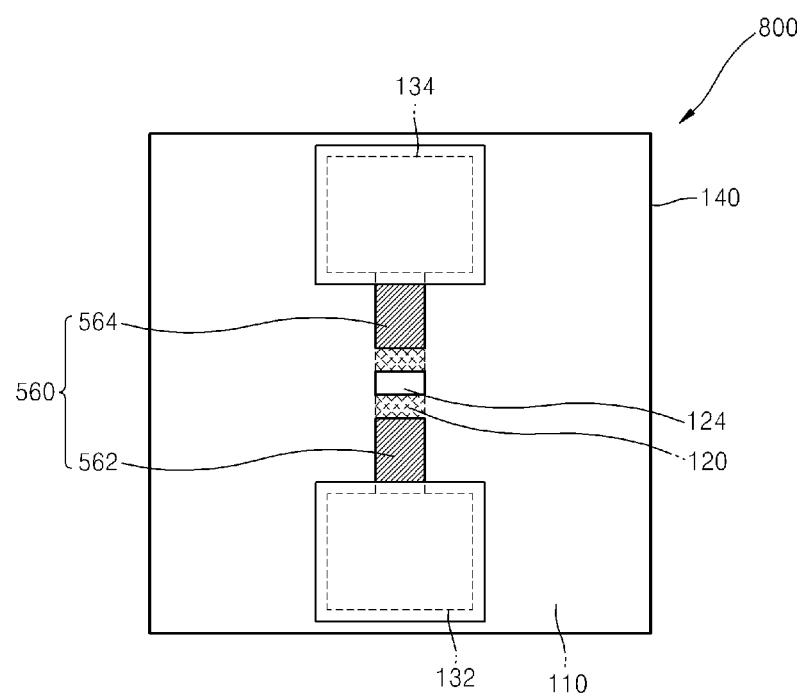

FIGS. 7A and 7B are a plan view and a cross-sectional view, respectively, illustrating a nanosensor 600 having a gap, according to an embodiment.

Referring to FIGS. 7A and 7B, the nanosensor 600 having a gap corresponds to the nanosensor 100 having a pore of FIGS. 1A and 1B. Plan views of the nanosensors 100 and 600 are slightly different from each other according to whether a pore is included or a gap is included.

Referring to FIGS. 7A and 7B, the nanosensor 600 having the gap 124 includes the first insulating layer 110 in which the first pore 112 is formed, and a graphene layer 120 disposed on the first insulating layer 110 and having a gap 124 formed therein proximal to face first pore 112. A size of the gap 124 may be determined according to a size of a target molecule to be detected or sequenced. Since the target molecule has to pass through the gap 124, a size of the gap 124 may be greater than a size of the target molecule. The size of the gap 124 may range from several nm to tens of nm. The gap 124 may be formed to face the first pore 112. Also, the size of the gap 124 may be equal to or less than a diameter of the first pore 112 and the gap 124 may partially overlap the first pore 112. The gap 124 may be formed by using, for example, an electron beam using a TEM, or by using an ion beam using FIB or RIE.

Suitable materials and sizes of the first and second insulating layers 110 and 140, the first and second electrode pads 132 and 134, and the substrate 150 of the nanosensor 600 having the gap 124 are the same as the suitable materials and sizes of the first and second insulating layers 110 and 140, the first and second electrode pads 132 and 134, and the substrate 150 of the nanosensor 100 having the second pore 122, and thus a detailed explanation thereof will not be given.

Also, the nanosensor 600 having the gap 124 may further include a marker element 160 that is disposed adjacent to the graphene layer 120 and which identifies a position of the graphene layer 120. The marker element 160 may be disposed on a portion of the first insulating layer 110 where the graphene layer 120 is not formed to be spaced apart from the graphene layer 120. For example, the marker element 160 may include the first and second markers 162 and 164 that are spaced apart from each other with the graphene layer 120 therebetween. A line that connects the first and second markers 162 and 164 may cross the graphene layer 120. For example, the line that connects the first and second markers 162 and 164 may pass through the gap 124. Each of the first and second markers 162 and 164 may have, but is not limited to, a bar shape having a long width parallel to the direction of the line that connects the first and second markers 162 and 164. The marker element 160 may be formed of a metal material, an insulating material, or a polymer. In various embodiments, the metal material may be any one selected from the group consisting of Au, Cu, Pd, Ni, Ti, Cr, FE, Co, Pt, Ru, and a mixture thereof.

An element of the nanosensor 600 is formed, for example, by using electron beam lithography, and then a nanogap is formed therein, for example, by using equipment such as an FIB tool or a TEM. In particular, a TEM is often used to manufacture a gap having a size equal to or less than several nm. In this case, it is difficult to identify a position of the graphene layer 120. Accordingly, the marker element 160 is additionally formed in order to identify a position of the graphene layer 120 even when a gap having a size of several nm is formed. The marker element 160 may be spaced apart by a distance equal to or less than hundreds of nm from the graphene layer 120.

FIGS. 8 through 11 are plan views illustrating nanosensors 700, 800, 900, and 1000, each having a gap, according to other embodiments.

The nanosensors 700, 800, 900, and 1000 each having a gap of FIGS. 8 through 11, respectively, correspond to the nanosensors 200, 300, 400, and 500 each having a pore of FIGS. 2A, 3A, 4 and 5. While the nanosensors 700, 800, 900, and 1000 of FIGS. 8 through 11 detect and sequence a target molecule by measuring tunneling current generated while the target molecule passes through a gap, the nanosensors 100 of FIGS. 2A, 3A, 4, and 5 detect or sequence a target molecule by measuring a change in electrical characteristics when the target molecule stops up or is positioned within a pore. Like a pore, a gap of each nanosensor may be formed by using a TEM, an FIB tool, or the like. However, a gap is different from a pore in that a gap divides a graphene layer into a plurality of distinct regions.

Since the second pore 122 and the gap 124 are regions where a target molecule is detected or sequenced, the second pore 122 and the gap 124 may be referred to as detection regions. It is difficult to form the second pore 122 and the gap 124 in the graphene layer 120 due to a limitation in a size of the graphene layer 120 and sizes of the second pore 122 and the gap 124. However, since the marker 260, 360, 460, or 560 for identifying a position of the graphene layer 120 is formed, the second pore 122 and the gap 124 may be formed more easily.

Such a marker is not limited to being used for only a nanosensor. The marker may be applied to any apparatus including a graphene layer in which identification of a position of the graphene layer (or other layer) is needed. Such an apparatus may be an electronic device such as a transistor including a graphene layer as well as a nanosensor. For example, when an apparatus including a graphene layer is manufactured, an element of the apparatus is formed, the graphene layer is formed on a first portion of the element, and a marker is formed on a second portion of the element or the graphene layer. Next, another element of the apparatus is formed, thereby manufacturing the apparatus including the graphene layer.

While the present invention has been particularly shown and described with reference to exemplary embodiments thereof, they are provided for the purposes of illustration and it will be understood by those of ordinary skill in the art that various modifications and equivalent other embodiments can be made from the present invention. Accordingly, the true technical scope of the present invention is defined by the technical spirit of the appended claims.

All references, including publications, patent applications, and patents, cited herein are hereby incorporated by reference to the same extent as if each reference were individually and specifically indicated to be incorporated by reference and were set forth in its entirety herein.

As used herein, the term "and/or" includes any and all combinations of one or more of the associated listed items. The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A nanosensor comprising:
a first insulating layer having a first pore formed therein;
a graphene layer disposed on the first insulating layer and having a second pore or a gap formed therein adjacent to the first pore; and
a marker element, including a marker material disposed on a portion of the first insulating layer where the graphene layer is not formed and wherein the marker element is spaced apart from the graphene layer.

2. The nanosensor of claim 1, wherein a size of the first pore is equal to or greater than a size of the second pore or a size of the gap.

3. The nanosensor of claim 1, wherein the second pore or the gap partially overlaps the first pore.

4. The nanosensor of claim 1, wherein the marker element comprises a first marker and a second marker spaced apart from each other with the graphene layer located therebetween.

5. The nanosensor of claim 4, wherein the first marker and second marker are disposed such that a line that connects the first marker and the second marker crosses the graphene layer.

6. The nanosensor of claim 4, wherein the first marker and second marker are disposed such that a line that connects the first marker and the second marker passes through the second pore or the gap.

7. The nanosensor of claim 4, wherein each of the first marker and the second marker is spaced apart by about 50 nm to about 500 nm from the second pore or the gap.

8. The nanosensor of claim 1, wherein the marker material includes a metal material, an insulating material, or a polymer.

9. The nanosensor of claim 1, further comprising a first electrode pad and a second electrode pad that are disposed on opposite sides of the graphene layer and spaced apart from each other.

10. The nanosensor of claim 9, further comprising a second insulating layer that covers the first electrode pad and the second electrode pad and that is disposed on the first insulating layer.

11. The nanosensor of claim 10, wherein the marker element is disposed on the second insulating layer.

12. The nanosensor of claim 11, wherein the marker element comprises a first marker and a second marker disposed on a portion of the second insulating layer where the second insulating layer does not overlap the graphene layer and wherein the first marker and the second marker are spaced apart from each other with the second pore or the gap therebetween.

13. The nanosensor of claim 11, wherein the marker element comprises a first marker and an second marker disposed on a portion of the second insulating layer where the second insulating layer overlaps the graphene layer and wherein the first marker and the second marker are spaced apart from each other with the second pore or the gap therebetween.

* * * * *